United States Patent [19]
Mata et al.

[11] Patent Number: 5,891,144
[45] Date of Patent: Apr. 6, 1999

[54] EXTERNAL FIXATOR

[75] Inventors: Jacques Mata; Marcel Nyfeler, both of Etoy; Denis Worek, Veyrier, all of Switzerland

[73] Assignee: Jaquet Orthopédie S.A., Switzerland

[21] Appl. No.: 843,420

[22] Filed: Apr. 15, 1997

[51] Int. Cl.[6] .................................................. A61B 17/56
[52] U.S. Cl. ................................ 606/59; 606/54; 606/57
[58] Field of Search .................................. 606/59, 57, 54; 403/133

[56] References Cited

U.S. PATENT DOCUMENTS

| | | | |
|---|---|---|---|
| 5,160,335 | 11/1992 | Wagenknecht | 606/59 |
| 5,207,676 | 5/1993 | Canadell et al. | 606/54 |
| 5,393,161 | 2/1995 | Mata et al. | 403/133 |

FOREIGN PATENT DOCUMENTS

3614305A1  11/1987  Germany.

Primary Examiner—Michael Buiz
Assistant Examiner—Julian W. Woo
Attorney, Agent, or Firm—Peter C. Richardson; Lawrence C. Akers; Raymond W. Augustin

[57] ABSTRACT

An external fixator including at least two groups of pins inserted respectively on either side of the fracture. Two vices are used for securing the pins to two hinge elements. The hinge elements are used to connect and orient the vices in relation to an external immobilizing rod which extends parallel to the bone. Each vice includes a clamping jaw and a bar intended to connect to one of the hinge elements.

5 Claims, 1 Drawing Sheet

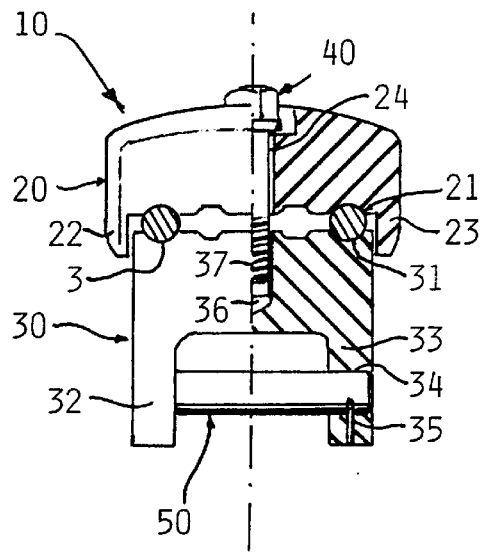
Fig. 1
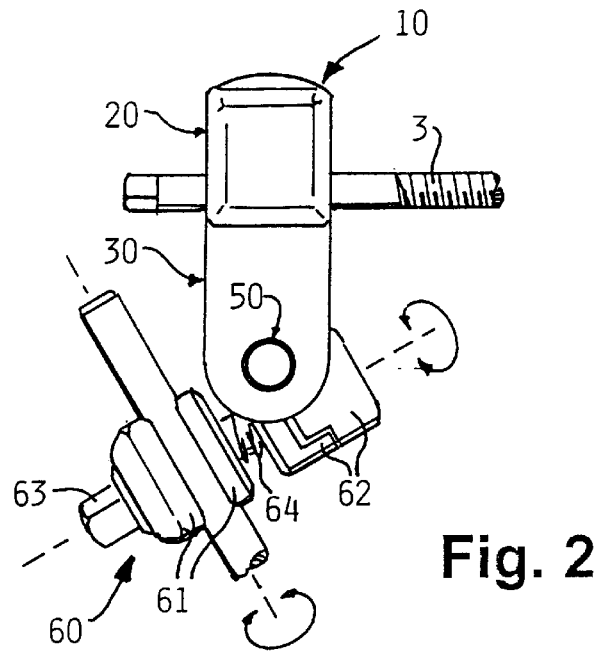
Fig. 2
Fig. 3
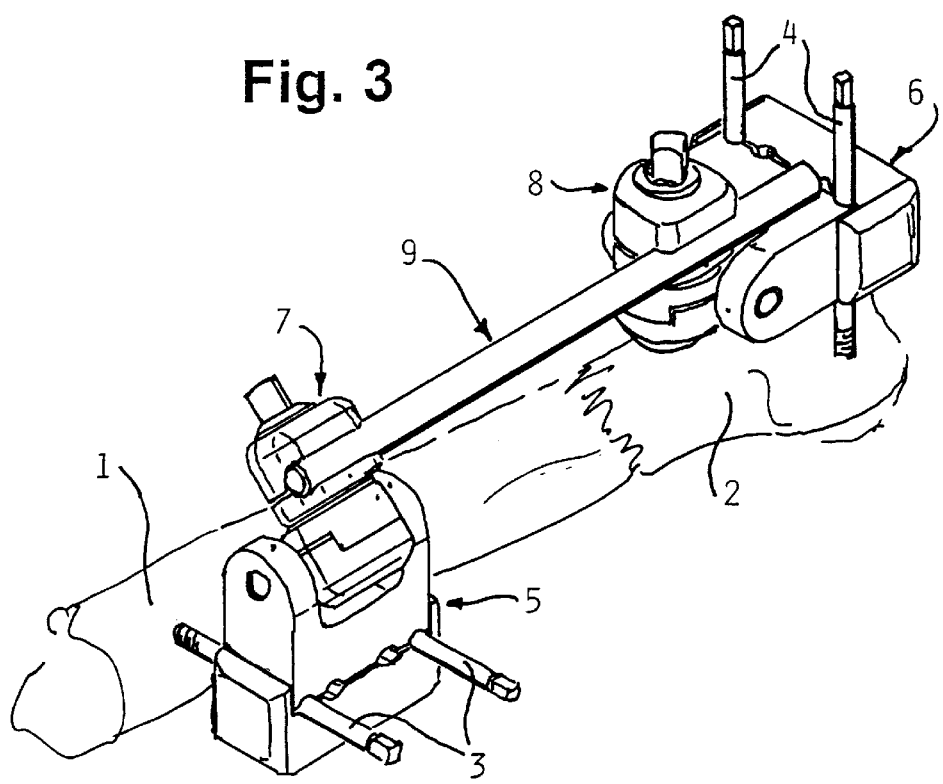

EXTERNAL FIXATOR

BACKGROUND OF THE INVENTION

1. Field of the Invention

The present invention pertains to the field of orthopaedics and relates more particularly to an external fixator which is intended for the consolidation of a long bone fractured towards its end.

2. Description of the Prior Art

For many years now, development work has been carried out on external fixators whose components are put into place after the pins have been inserted in the optimum position in relation to the bone fragment, which is to be maintained, and to the tissue surrounding it. Hinge elements provide for the connection between the pins and the immobilizing rod or rods, so as to ensure their relative orientation.

The Applicant has specifically developed for this purpose the hinge element which is described in U.S. patent application Ser. No. 08/788,718, filed Jan. 24, 1997, the teachings of which are incorporated herein by reference and which permits orientation either of a pin and a rod or of two rods. This hinge element includes several pairs of jaws forming grooves which are positioned and disposed in such a way as to present an external opening which allows the cylindrical component or rod to be snapped into place by means of pressing them against to the elastic or spring means. The spring presses the adjacent faces of the jaws against the cylindrical components prior to the hinge element being locked.

In some cases it is necessary to use a fixator which includes a single immobilizing frame. For this type of fixator, pairs of at least two bone pins are inserted on either side of the fracture and are indirectly fixed to the ends of an immobilizing rod. When a long bone is fractured near a joint, it is preferable to insert the pins in what is called a "T" arrangement, some of the pins being inserted in the epiphysis in a plane perpendicular to the bone, the others being inserted in the central part of the bone, in a plane containing the fractured bone. Each group of pins is held in a vice which can be oriented in relation to the immobilizing rod by means of a hinge or a ball joint.

SUMMARY OF THE INVENTION

The present invention aims to simplify this type of fitting and to reduce the size and weight of the assembly, more particularly designed for long bones, such as the radius, which have been fractured near their end. The subject of the invention is a fixator comprising at least:

two groups of pins inserted respectively on either side of the fracture, two vices for securing the pins, two hinge elements providing for orientation of the vices in relation to an immobilization rod.

The fixator of the present invention is characterized by the fact that one of the jaws of each vice includes a small cylindrical bar intended to cooperate with a hinge element.

The invention also extends to a procedure for putting the fixator according to the invention into place and for positioning the bone fragments by virtue of the combination of rotational movement.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 represents the vice according to the invention, in a front view on the left-hand side of the drawing and in cross-section on the right-hand side;

FIG. 2 represents the vice in FIG. 1 as seen from the side and shown mounted on a hinge element of the type which is described in detail in U.S. patent application Ser. No. 08/788,718; and FIG. 3 is a perspective view of the fixator assembly according to the invention.

DESCRIPTION OF THE PREFERRED EMBODIMENT

The vice 10 represented in FIG. 1 consists in a conventional manner of an upper jaw 20 and of a lower jaw 30 which are connected by a central locking screw 40. These jaws 20 and 30 include series of parallel grooves 21 and 31 for the bone pins 3.

The upper jaw 20 additionally includes two wings 22 and 23 for relative positioning of the jaws and a central passage 24 through which the locking screw 40 passes freely.

The lower jaw 30 has a generally "U" shape (upside down in the drawing), the branches 32 and 33 of which are intended to receive a small bar 50 whose ends are inserted in a bore 34 formed in each branch and are secured by means of a small pin 35 intended to prevent any rotation of the small bar. The lower jaw 30 also includes a central bore 36 intended to cooperate with the screw 40. A threaded metal socket 37 is preferably formed within bore 36 for receiving screw 40. A small bar 50 is parallel to the plane containing the pins and, as can be seen in the drawing, is perpendicular to the axis of the bone pins.

The side view in FIG. 2 again shows jaws 20 and 30 forming vice 10 for clamping pins 3. The lower jaw 30 presenting bar 50 intended for securing a hinge element 60. The latter includes a first pair of jaws 61 which are clamped on a spacing rod and a second pair of jaws 62 clamped on bar 50, it being possible for these pairs of jaws to be oriented in relation to a central axis constituted by the locking screw 63 which constitutes the axis of rotation of the jaws. It is possible to separate the pairs of jaws 61 and 62 by a helical spring 64 which is intended to hold the components in place until the screw 63 has been fully tightened, as is detailed in U.S. patent application Ser. No. 08/788,718. Bars 50 and spacing rod 9 preferably having the same diameter, thereby permitting greater freedom in the positioning of the components.

The general view in FIG. 3 shows a long bone 1 such as the ulna which has been fractured relatively close to the distal end 2 of the radius, an area where more than 20% of limb fractures occur. Each bone fragment 1 and 2 receives at least two pins 3 and 4, respectively, which are preferably disposed in a "T" arrangement. These pins are clamped in two vices 5 and 6 cooperating with hinge elements 7 and 8 between which an immobilizing rod 9 is disposed. The physician will be able to reduce the fracture and return the bone fragments 1 and 2 to their optimum position by virtue of the combination of the rotational movements of:

the hinge elements 7 and 8 in relation to the axis of the rod 9, the pairs of jaws of each hinge element 7 or 8 on their clamping axis 63, the hinge elements 7 and 8 in relation to the small bar of each vice 5 or 6.

In the representation in FIG. 3, the pins 3 are in a horizontal plane, while the pins 4 are in a vertical plane. It will be noted that the axis of the hinge element 8 is substantially parallel to the pins 4, while the axis of the hinge element 7 is at 45° to the plane containing the pins 3.

In the case of fractures of the wrist, it has been observed that it is of advantage to dispose the pins 3 preferably in a plane at 45° to the horizontal, the axis of the hinge element 7 being substantially aligned with the central clamping axis of the vice 5. Depending on the region of use of the fixator according to the invention, it is possible to envisage arranging the two groups of pins in substantially parallel planes, and not in the "T" arrangement as is described above, without departing from the scope of the present invention.

The procedure for attaching the fixator described hereinabove consists of inserting pairs of pins into the bone fragments on either side of the fracture. Then the pins are clamped in the vices and the hinge elements are fitted on the vices and on an immobilizing rod. Then the final adjustment of the position of the bone fragments is accomplished by virtue of the combination of the rotational movements of the hinge elements, or in other words, positioning of the immobilizing rod in relation to the pins.

It is also to be noted that it is advantageous to use vices, and even an immobilizing rod, made of radio-transparent, composite materials, so that it is easy to check the relative positioning of the bone fragments when the fixator is being put into place. For example, use will be made of reinforced plastics, preferably ones based on carbon fibers.

We claim:

1. An external fixator for attachment to a fractured bone comprising:

two groups of at least two pins having first ends insertable into the bone on either side of the fracture;

two vice elements clamped to second ends of each group of pins, each vice element having a first jaw for clamping onto said pins and each vice element further including a cylindrical bar, said bar on said vice element extending in a direction perpendicular to a longitudinal axis of said pins;

an immobilizing rod extendable across the fracture;

a pair of hinge elements, each having two pairs of rotatable clamps for respectively engaging said immobilizing rod and said cylindrical bar; and each vice element includes a second jaw in the shape of a U having branches including two openings which face each other into which ends of said cylindrical bar are inserted.

2. The fixator as set forth in claim 1 wherein said opening in said branch additionally includes an element for locking the bar against rotation.

3. The fixator as set forth in claim 1 wherein the jaws of the vice are made of reinforced plastic.

4. A method for attaching an external fixator to a fractured bone according to claim 1, comprising the steps of:

inserting each group of pins into bone fragments on either side of the fracture;

clamping the pins in the vice elements; and fitting the hinge elements onto the cylindrical bar of the vices and onto said immobilizing rod prior to proceeding to the final adjustment of the position of the bone fragments by positioning the immobilizing rod in relation to the pins.

5. The method as set forth in claim 4 wherein the two groups of pins are arranged with one group of pins being inserted in a first plane and the other group of pins being inserted in a plane oriented perpendicularly to said first plane.

* * * * *